(12) United States Patent
Griffiths et al.

(10) Patent No.: US 6,748,263 B2
(45) Date of Patent: Jun. 8, 2004

(54) MONITORING ELECTRICAL ACTIVITY

(75) Inventors: Mark James Griffiths, Clifton upon Teme (GB); Alan W Preece, Bristol (GB)

(73) Assignee: The University of Bristol, Bristol (GB)

( * ) Notice: Subject to any disclaimer, the term of this patent is extended or adjusted under 35 U.S.C. 154(b) by 51 days.

(21) Appl. No.: 10/203,954

(22) PCT Filed: Feb. 16, 2001

(86) PCT No.: PCT/GB01/00629

§ 371 (c)(1),
(2), (4) Date: Oct. 8, 2002

(87) PCT Pub. No.: WO01/60252

PCT Pub. Date: Aug. 23, 2001

(65) Prior Publication Data

US 2003/0109796 A1 Jun. 12, 2003

(30) Foreign Application Priority Data

Feb. 17, 2000 (GB) ................................................ 0003665

(51) Int. Cl.⁷ .................................................. A61B 5/04
(52) U.S. Cl. ........................ 600/544; 600/300; 600/509; 600/546
(58) Field of Search ................................. 600/300–301, 600/500–505, 544–546

(56) References Cited

U.S. PATENT DOCUMENTS

| 4,846,190 A | | 7/1989 | John | |
| 5,109,863 A | * | 5/1992 | Semmlow et al. | 600/528 |
| 5,211,179 A | * | 5/1993 | Haberl et al. | 600/515 |
| 5,299,118 A | | 3/1994 | Martens et al. | |
| 5,458,117 A | | 10/1995 | Chamoun et al. | |
| 5,765,128 A | | 6/1998 | Tsuboi et al. | |
| 5,938,594 A | * | 8/1999 | Poon et al. | 600/300 |
| 5,940,798 A | * | 8/1999 | Houde | 704/271 |
| 6,011,990 A | | 1/2000 | Schultz et al. | |

* cited by examiner

*Primary Examiner*—Charles Marmor
*Assistant Examiner*—Patricia C. Mallari
(74) *Attorney, Agent, or Firm*—Reising, Ethington, Barnes, Kisselle, P.C.

(57) ABSTRACT

A method and apparatus for monitoring electrical activity, such as brainwaves, in an animal comprising detecting said activity to produce a corresponding output signal, combining the output signal with a random noise signal to produce a modified signal, and analyzing the modified signal using an autocorrelation technique to detect the relative power density values at a plurality of different frequencies. The random noise signal may be a random number. The autocorrelation technique may involve the Yule-Walker method.

28 Claims, 2 Drawing Sheets

MONITORING ELECTRICAL ACTIVITY

The present invention relates to a method of monitoring electrical activity in an animal, especially human brain waves, and apparatus for carrying out the method such as an electroencephalograph.

It has been found that when a person is sedated, but not yet anaesthetised, their brain waves contain a frequency component which occurs between 8 and 12 Hz, and is known as the alpha rhythm. As sedation passes to full anaesthesia, the alpha rhythm disappears on termination of anaesthesia as the person returns to a sedated state, it reappears and then tends to disappear again when the person is fully awake.

It has been realised that this effect may be used to detect any undesired transition from anaesthesia to sedation, corresponding to the person beginning to regain consciousness, for example when a surgical operation is taking place. However, the emergence of the alpha rhythm, as anaesthesia passes to sedation, represents a small component in the total brain wave spectrum, and it has not proved possible using known methods to detect the gradual appearance of the alpha rhythm.

In addition, the occurrence of new frequencies lower than the alpha band such as delta, induced by the anaesthetic agent can be used to detect the undesirable presence of true anaesthesia if the intention is to maintain a state of sedation.

Known methods of analysing brain waves via electroencephalographs analyse the brain wave spectra using Fast Fourier Transforms. However, in detecting a weak frequency component, corresponding to the emerging alpha rhythm or low frequency delta rhythm induced by an anaesthetic agent, the use of a Fast Fourier Transform is unsuitable. There are two reasons for this. Firstly, noise in the brain wave signal is analysed by the Fast Fourier Transform as corresponding to many weak frequency components. It is thus not easy to distinguish between weak frequency components due to noise, and weak frequency component due to other reasons, such as the emergence of the new frequencies. Secondly, unless the frequency component being detected corresponds to one of the sampling frequencies of the Fast Fourier Transform, the Fast Fourier Transform will tend to split a frequency signal into a range of spurious frequency components.

The result of these two effects is that the Fast Fourier Transform tends to mask weak components. Hence, it is unsuitable for detecting the emergence of the alpha rhythm. By the time that the alpha rhythm for example is sufficiently significant to be detectable by Fast Fourier Transform, the person will have passed from anaesthesia to sedation, so that it is not possible in this way to carry out early detection of that transition.

Therefore, the present invention seeks to provide an apparatus and a method, of analysing brain waves which permits these rhythms to be detected when they are very weak. This then permits an indication of the anaesthesia or sedation level to be determined. However, as will be explained below, the present invention is not limited to detection of alpha and lower rhythms and could be used to detect other components such as epileptic spikes in the brain wave signal.

According to the present invention, electrical activity is detected and produces a corresponding output signal, the output signal is combined with a random noise signal to produce a modified signal, and the modified signal is analysed using an autocorrelation technique to detect the relative power density values at a plurality of different frequencies.

Preferably, the autocorrelation technique involves use of the Yule-Walker algorithm.

The value of one or more power density values at a frequency or frequencies corresponding to a specific rhythm such as the alpha or delta is then compared with the sum of the power density values over a wider range of frequencies. The result of this comparison gives a measure which may be used to detect the emergence of these rhythms. To express this in another way, the relative power density $D_f$ at various frequency f are derived using Equation 1 below, for a multiplicity of frequencies f.

$$D_f = \frac{1}{\left|1 + \sum_{p=1}^{M} y_p \exp(-i \cdot a \cdot f \cdot p)\right|^2} \qquad \text{Equation 1}$$

where $y_p$ is the pth Yule-Walker coefficient, and a is a constant.

Then, the ratio of the sum of one or more values of $D_f$ at or about the frequencies of the particular rhythms are compared with the sum of the values of $D_f$ over a wider range of values, and the changes in that ratio may be used to detect the emergence of these rhythms.

In general, the maximum frequency of the wider range will be at least approximately double that of the maximum frequencies of the rhythms under consideration.

It should be noted that Yule-Walker methods from which the Yule-Walker coefficients referred to in Equation 1 above are obtained, are a known type of frequency analysis method. For a detailed discussion of Yule-Walker methods, reference may be made to the book "Digital Signal Processing" (second edition) by J G Proakis and D G Manolakis published by McMillan publishing company, New York.

The present invention also consists in an electroencephalograph which monitors brain waves using the method discussed above, to indicate the emergence of specific rhythms, and also consists in a method of operation such as an electroencephalograph.

In order to derive the Yule-Walker coefficients referred to above, the present invention further proposes that a series of autocorrelation products be derived from the brain wave signals. These autocorrelation products may then be used directly, to derive the Yule-Walker coefficients, but it is preferable that an averaging technique is applied to them. It would be possible to determine the autocorrelation direct over a relatively long time period, but it is preferable to use a shorter time period and average over those time periods. The advantage of this is that short bursts of noise are then not carried over from one period to the next. Averaging in this way has the disadvantage of slowing detection of trends, and therefore there is the need to compromise between these factors.

In deriving the autocorrelation products, it has been found advantageous to add random linear noise to the brain wave signals. Provided that the amount of random linear noise added is not too great. the reduction in spectral resolution which results is not of practical consequence. However, it has been found that the addition of such random linear noise tends to reduce or prevent the occurrence of occasional rogue results. It is also preferable that any DC components of the brain wave signals be removed, to counteract the effect of drift.

In order to carry out the analysis of the brain waves as discussed above, an electroencephalograph according to the present invention preferably converts the brain wave signals to digital signals, to enable those signals to be analysed by a suitably programmed processor. The analysis of the relative power density values may then be used to generate a suitable display and/or audible signal, and/or a control signal for other equipment. In fact, it is preferable that the value corresponding to the comparison of relative power densities discussed above is converted to an index value which is a non-linear function of the initial value, to emphasise changes at low values of the specific rhythm.

An embodiment of the present invention to define the occurrence of the alpha rhythm will now be described in detail, by way of example, with reference to the accompanying drawings, in which.

Figure 1:
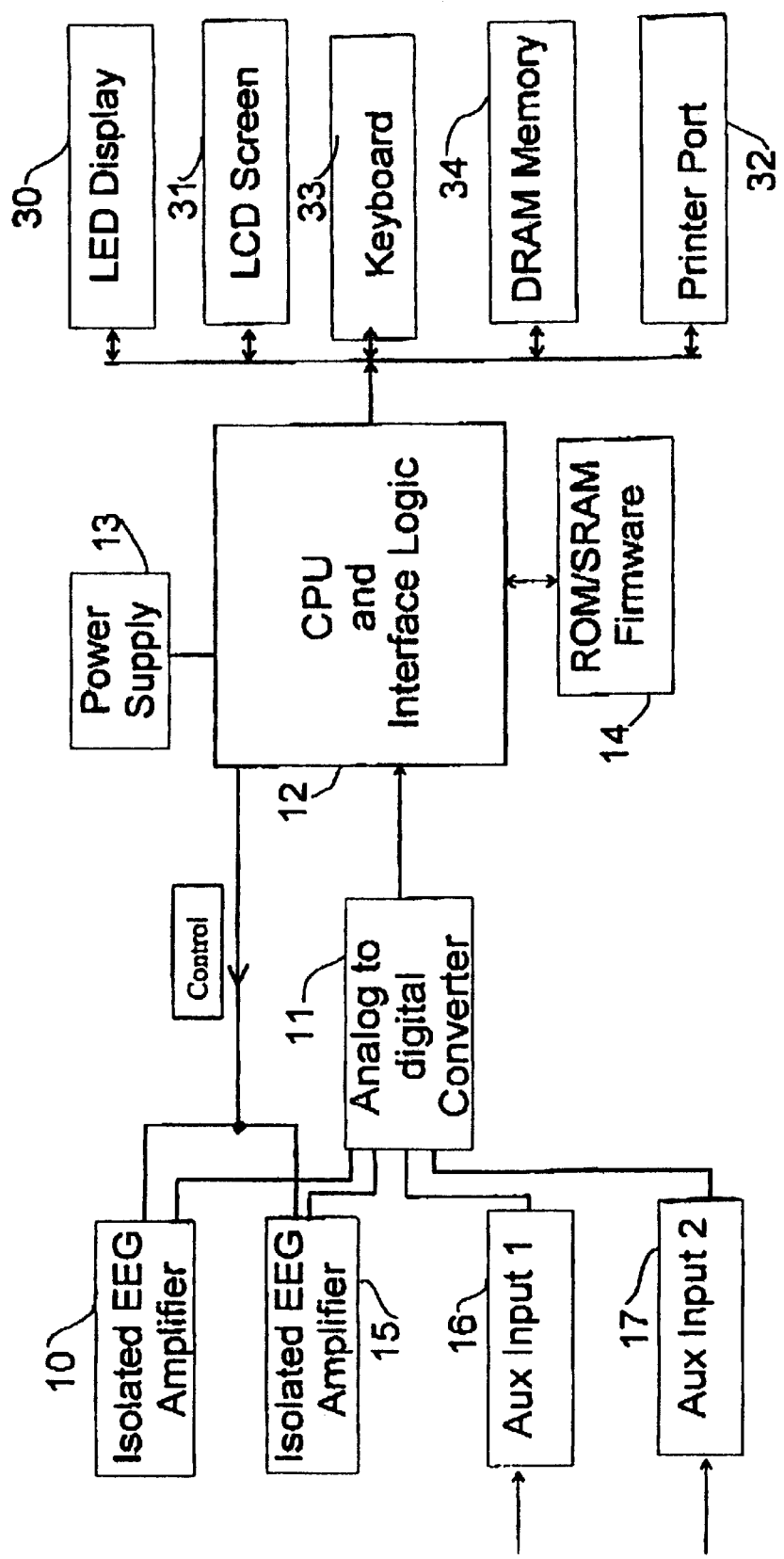
FIG. 1 shows an electroencephalograph being an embodiment of the present invention.

Referring first to FIG. 1, an electroencephalograph amplifier unit 10 generates electrical signals corresponding to the brain waves, and passes those signals to an analogue-to-digital converter 11. The resulting digital signals are passed to a processor 12, in which they are processed using a Yule-Walker method, as will be described in more detail later.

Figure 2:
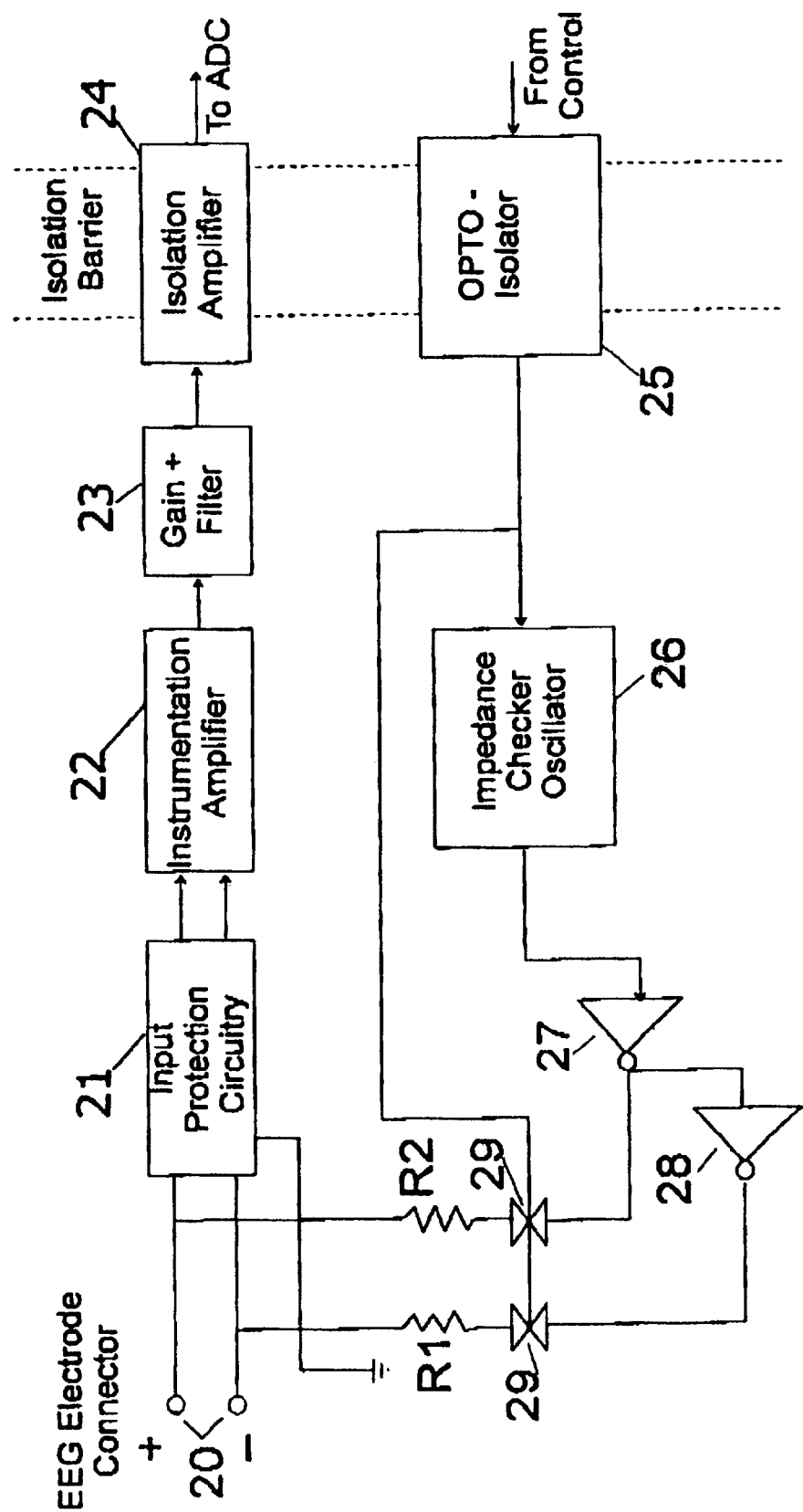
FIG. 2 shows part of the electroencephalograph of FIG. 1.

The structure of the amplifier unit 10 is shown in more detail in FIG. 2. Electrodes 20, for attachment to a person whose brain waves are to be investigated, are connected to an input protection circuitry unit 21 which protects other parts of the electroencephalograph from damage due to high voltage discharge. The input protection circuitry unit 21 may also act to protect the person to whom the electrodes 20 are connected from failures within the electroencephalograph. As can be seen from FIG. 2, the input protection circuitry unit 21 is also connected to ground, so that it passes differential signals to an amplifier unit 22. That amplifier unit removes common mode noise, and produces a single signal from the input thereto which is then passed to a gain and filter unit 23. The gain and filter unit 23 removes high frequency and DC components from the signal, and further amplifies the signal before it is passed to an isolation amplifier unit 24. That isolation amplifier unit 24 acts as a isolation barrier between the electroencephalograph amplifier 10 and the analogue to digital converter 11.

As shown in FIG. 1 the processor 12 is powered from a power supply unit 13, which may contain a mains connection and a battery back-up so that the power is uninterruptable. The program for controlling the processor 12 during operation is stored in a memory unit 14.

Furthermore, as is also shown in FIG. 1, the processor 12 may be connected to a second electroencephalograph amplifier unit 15, by the analogue digital converter 11. That second electroencephalograph amplifier 15 may have the same structure as shown in FIG. 2. Two auxiliary inputs 16, 17 may be provided to allow digitisation of non-isolated inputs from a CAPNOGRAPH or similar equipment.

FIG. 1 also shows that a signal is passed from the processor 12 to the electroencephalograph amplifiers 10, 15. This signal is an enabling signal which is passed via an opto-isolator unit 25 (see FIG. 2) to an impedance checker oscillator 26 of the electroencephalograph amplifier 10, 15. The opto-isolator unit 25 thus provides electrical safety isolation between the processor 12 and the electroencephalograph amplifier unit 10, 15, in a similar way to the isolation amplifier unit 24. When the impedance checker oscillator 26 is enabled by the signal from the processor 12, it outputs a frequency signal of between e.g. 5 and 10 Hz which is passed via two operational amplifiers 27, 28 to generate two signals which are passed via transmission gates 29 to respective resistors R1, R2. The resulting signal may be used to assess the input impedance of the electrodes 20.

It can be seen from FIG. 2 that the transmission gates 29 are enabled by the signal from the processor 12, which is output from the opto-isolator 25. The processing carried out by the processor 12 will now be described in more detail.

As was mentioned above, the present invention makes use of a Yule-Walker method to derive relative power density values. However, it should be noted that theoretical frequency analysis using such methods normally assume steady state conditions, which do not apply to brain wave signals. In fact, the consistent frequencies of such signals are often strongly amplitude modulated. Irregular waxing and waning occurs for some or all of the frequencies with successive maxima intervals varying within a range of half a second to two seconds. Furthermore, eye movements of the person to whom the electrodes 20 are connected can cause large irregular voltage excursions, and it has also been found that there are other non-periodic components. There may also be low frequency or DC drift. Hence, in applying a Yule-Walker method to brain wave signals, it is preferable that the processor 12 makes use of practical compromises as discussed below.

In the following discussion, various specific values are used to describe the analysis method. However, the present invention is not limited to these specific values.

The processor 12 analyses the signals corresponding to the brain waves in a series of time periods (epochs). The length of time period need not be fixed, and indeed an electroencephalograph according to the present invention may permit the duration of the epochs to be varied. However, an epoch of about 1.5 s duration has been found to be suitable. Assuming that the sampling rate of the processor 12 was e.g. 128 Hz, this would result in 192 sample values. This can be generalised, however, to N sample values per epoch, being:

$a_0, a_1, \ldots a_{n-1}$

It has been found that it is then preferable to add random linear noise to each of these sampled values, it has been found that if this is not done, consistent results cannot be ensured. Occasional rogue results may be detected which are sufficiently different from those of adjacent epochs to cause inaccurate analysis. Although addition of a random value reduces the spectral resolution that can be obtained, it is possible by suitable selection of the random value, to reduce the requisite error without the reduction of spectral resolution being of practical significance. The consequence of not adding noise in the form of random values is that the frequencies of interest can become too small in comparison to the totality of the other frequencies to be detected at times of high input noise or large DC offsets before these can be removed by averaging. Thus, in this embodiment, a modified sampled value $a'_k$, may be obtained, as follows.

$$a'_k = a_k + \text{abs}\left(\frac{a_{\max}}{20000}\right)(500 - \text{random}(1000)) \qquad \text{Equation 2}$$

In equation 2, $a_{max}$ is the numerically greatest sampled value in the epoch, and "random (1000)" is a random positive integer in the range of 0 to 1000. Such a random positive integer may be obtained from a pseudo-random program of the processor 12.

There may be a DC component imposed on the brain wave signals, and this DC component may include a drift component. To remove this effect, the average value of $a'_k$ over all the n values is subtracted from each value $a'_k$ to derive a further modified value $a''_k$. This process can be carried out for each epoch, and it should be noted that the addition of the random value discussed above does not introduce a further bias.

Next, a series of autocorrelation products must be derived. The number of autocorrelation products that need to be derived depend on the order of the Yule-Walker method used. Assuming that order is m, m+1 autocorrelation products will be derived. In practice, values of m between 40 and 50 have been found to give satisfactory results. Then, each autocorrelation product $x_p$ is given by equation 3 below:

$$x_p = \frac{1}{n-p} \sum_{k=0}^{n-p-1} a''_k a''_{k+p} \qquad \text{Equation 3}$$

In this equation p is the number of the autocorrelation product, varying between 0 and m. The values of $x_p$ are then a measure in the time domain of the periodic components of the brain wave signals.

Although it is then possible to use those autocorrelation products $x_0 \ldots x_m$ to derive Yule-Walker coefficients, it is preferable first to apply an averaging effect across a plurality of epochs. It has been found that computing autocorrelation over short epochs, and then carrying out an averaging operation, is better than calculating the autocorrelation products directly over longer epochs. Short epochs allow for drift correction, and short bursts of noise do not carry over. Thus, averaging reduces the effect of irregularities in the brain wave signals, but slows the detection of trends.

A compromise needs to be found between these factors, and it has been found that maintaining a running average, over 12 s is a satisfactory compromise. If 1.5 s epochs are used, as mentioned above, then averaging is over 8 epochs. Then, a new running average $R_p$ is derived from the previous running average $R'_p$ by equation 4 below.

$$R_p = \frac{7R'_p + x_p}{8} \qquad \text{Equation 4}$$

Since the running averages $R_p$ of the autocorrelation products are dated for each epoch, they are at any time available for analysis of the brain wave signals. In order to carry out that analysis, it is necessary to solve Equation 5 below.

$$\begin{bmatrix} R_0 & R_1 & \cdots & R_{M-1} \\ R_1 & R_0 & \cdots & R_{M-2} \\ \vdots & \vdots & & \vdots \\ R_{M-1} & R_{M-2} & \cdots & R_0 \end{bmatrix} \begin{bmatrix} Y_0 \\ Y_1 \\ \vdots \\ Y_M \end{bmatrix} = - \begin{bmatrix} R_1 \\ R_2 \\ \vdots \\ R_M \end{bmatrix} \qquad \text{Equation 5}$$

In equation 5, $y_0$ to $y_m$ are the Yule-Walker coefficients.

Although Equation 5 above can be solved in any satisfactory way, it has been found that the Levinson-Durbin solution algorithm may be used, as this enables the equation to be solved rapidly.

If the sampling rate is at 128 points per second, as previously mentioned, the relative power density $D_f$ at a frequency f is then given by Equation 6 below.

$$D_f = \frac{1}{\left| 1 + \sum_{p=1}^{M} y_p \exp\left(-i \cdot \frac{2\pi f}{64} \cdot p\right) \right|^2} \qquad \text{Equation 6}$$

It should be noted that since the analysis that is subsequently used in this embodiment makes use of ratios, rather than absolute values, the numerator in the above equation has been set to 1.

It is convenient to evaluate the relative power density values $D_f$ at intervals of e.g. a quarter Hz.

Then, a ratio $\alpha_r$ can be derived from equation 7.

$$a_r = \left\{ \sum_{k=32}^{48} D_{(k/4)} \right\} \Big/ \left\{ \sum_{k=2}^{96} D_{(k/4)} \right\} \qquad \text{Equation 7}$$

On the right hand side of this equation, the numerator represents the sum of the relative power density values within the 8 to 12 Hz frequency range in which alpha rhythms occur, whilst the denominator is a sum of the relative power density values over a frequency range of 0.5 to 24 Hz. Hence, $\alpha_r$ gives a measure of the power density within the range corresponding to alpha rhythms, relative to a much wider frequency range encompassing the range of frequencies corresponding to the alpha rhythms. Thus, variations in $a_r$ represent variations in the power present in alpha rhythms.

Since the present invention seeks to detect the emergence of a specific rhythms, it is more important to detect change of $\alpha_r$, from e.g. 0.02 to 0.05 than to detect a change from 0.2 to 0.3. Therefore, in a final step, the processor may derive a value $\alpha_i$ which is a non linear function of $\alpha_r$ according to Equation 8.

$$\alpha_i = exp\{S. \ln(\alpha_r)\} \qquad \text{Equation 8}$$

In Equation 8, S is a sensitivity factor. If S equals 1,$\alpha_i$ and $\alpha_r$ would be the same. In practice, S equals 0.4 is a suitable value.

Once the processor 12 in FIG. 1 has derived the value $\alpha_i$ as discussed above, that value may be used to control. a display which the operator of the encephalograph may use to detect the emergence of a rhythm. For example as shown in FIG. 1, a signal may be passed to a LED display 30 which displays the current value of $\alpha_i$. In addition, or as an alternative, $\alpha_i$ may be presented as a vertical bar on an LCD screen 31, to give a graphical indication of variations in that value. Information may also be passed via a printer port 32 either directly to a printer, or to a suitable computer for further analysis. FIG. 1 also shows that the processor 12 is connected to a key board 33 which permits the operator to control the electroencephalograph, for example to input parameters such as the duration of each epoch. The processor 12 is also connected to a dram memory 34 which permits some data to be stored whilst the electroencephalograph is powered up.

It should be noted that calculation of $a_i$ requires the solution of Equation 5. Therefore, that equation could be solved every epoch, enabling the displays 30, 31 to be updated every 1.5 s. In practice, such an updating rate is not essential, and the processing load on the processor may be reduced by solving equation 8 e.g. every 3 epochs, to give an update of the displays 30, 31 every 4.5 s.

Furthermore. it can be seen from Equation 7 that suitable selection of the ranges of the values k in the numerator and denominator of that equation will enable the power of other frequency components to be investigated. Hence, although the present invention has been developed primarily to detect alpha rhythms occurring in the 8 to 12 Hz frequency range, the present invention may be applied to the analysis of other frequency components.

What is claimed is:

1. A method of monitoring electrical activity in an animal comprising detecting said activity to produce a corresponding output signal, combining the output signal with a random noise signal to produce a modified signal, and analyzing the modified signal using an autocorrelation technique to detect the relative power density values at a plurality of different frequencies.

2. A method as claimed in claim 1 in which the output signal is sampled at intervals.

3. A method as claimed in claim 2 in which the samples $a_k$ of the output signal are digital samples.

4. A method as claimed in claim 3 in which the random noise signal consists in a random number that is added to each sample $a_k$.

5. A method as claimed in claim 4 in which successive samples are averaged over an epoch and the average $a_k'$ subtracted from each sample $a_k$ to produce a modified sample $a_k''$.

6. A method as claimed in claim 4 in which the samples $a_k$, $a_k''$ are processed to derive a number of autocorrelation products $x_p$, using the Yule-Walker method.

7. A method as claimed in claim 6, in which $$x_p = \frac{1}{n-p} \sum_{k=0}^{n-p-1} a_k'' a_{k+p}''$$

where p is the number of the autocorrelation product between 0 and m.

8. A method as claimed in claim 7 in which the autocorrelation products $x_0$ to $x_m$ are averaged over successive epochs.

9. A method as claimed in claim 8 in which a running average $R_p$ of the autocorrelation products is derived from the averages of successive epochs.

10. A method as claimed in claim 8 in which the averaged autocorrelation products are analysed according to the Yule-Walker equation to derive Yule-Walker coefficients $y_o$ to $y_m$.

11. A method as claimed in claim 10 in which the Levinson-Durbin algorithm is used to derive the Yule-Walker coefficients $y_0$ to $y_m$ from the Yule-Walker equation.

12. A method as claimed in claim 10 in which the Yule-Walker coefficients are used to derive the relative power density $D_f$ at a frequency f of the output signal, where $$D_f = \frac{1}{\left|1 + \sum_{p=1}^{M} y_p \exp(-i \cdot a \cdot f \cdot p)\right|^2}$$

13. A method as claimed in claim 12 in which the relative power density $D_f$ is derived for multiple frequencies of the output signal, and the relative power density $D_f$ at one frequency or over a first range of frequencies is compared with the power densities $D_f$ over a wider range of frequencies to detect a change in power density at said one frequency or first range of frequencies.

14. A method as claimed in claim 1 applied to the monitoring of brain waves.

15. Apparatus for monitoring electrical activity in an animal comprising a detector to produce an output signal corresponding to the electrical activity, a random noise generator to produce a random noise signal, and a processor to combine the output signal and random noise signal to produce a modified signal and to analyse the modified signal using an autocorrelation technique to detect the elative power density values at a plurality of different frequencies.

16. Apparatus as claimed in claim 15, in which the processor samples the output signal at intervals.

17. Apparatus as claimed in claim 16 in which the processor samples digital samples $a_k$ of the output signal.

18. Apparatus as claimed in claim 17 in which the random noise generator produces a random noise signal in the form of a random number that is added to each sample $a_k$.

19. Apparatus as claimed in claim 18 in which the processor averages successive samples over an epoch and subtracts the average $a_k'$ from each sample $a_k$ to produce a modified sample $a_k''$.

20. Apparatus as claimed in claim 18 in which the processor processes samples $a_k$, $a_k''$ to derive a number of autocorrelation products $x_p$ using the Yule-Walker method.

21. Apparatus as claimed in claim 20, in which $$x_p = \frac{1}{n-p} \sum_{k=0}^{n-p-1} a_k'' a_{k+p}''$$

where p is the number of the autocorrelation product between 0 and m.

22. Apparatus as claimed in claim 21 in which the autocorrelation products $x_o$ to $X_m$ are averaged by the processor over successive epochs.

23. Apparatus as claimed in claim 22 in which a running average $R_p$ of the autocorrelation products is derived by the processor from the averages of successive epochs.

24. Apparatus as claimed in claim 22 in which the averaged autocorrelation products are analysed by the processor according to the Yule-Walker equation to derive Yule-Walker coefficients $y_o$ to $y_m$.

25. Apparatus as claimed in claim 24 in which the processor uses the Levinson-Durbin algorithm to derive the Yule-Walker coefficients $y_o$ to $y_m$ from the Yule-Walker equation.

26. Apparatus as claimed in claim 24 in which the processor uses the Yule-Walker coefficients to derive the relative power density $D_f$ at a frequency f of the output signal, where $$D_f = \frac{1}{\left|1 + \sum_{p=1}^{M} y_p \exp(-i \cdot a \cdot f \cdot p)\right|^2}$$

and a is a constant and M is the order of the Yule-Walker equation.

27. Apparatus as claimed in claim 26 in which the processor derives the relative power density $D_f$ for multiple frequencies of the output signal, and compares the relative power density $D_f$ at one frequency or over a first range of frequencies with the power densities $D_f$ over a wider range of frequencies to detect a change in power density at said one frequency or first range of frequencies.

28. An electroencephalograph comprising apparatus as claimed in claim 15.

* * * * *